(12) United States Patent
Marshall et al.

(10) Patent No.: US 7,153,318 B2
(45) Date of Patent: Dec. 26, 2006

(54) INTEGRATION OF A LANCETTE WITH ITS CAPTURING AND REMOVING CAP

(75) Inventors: Jeremy Marshall, Oxford (GB); David Danvers Crossman, Oxford (GB)

(73) Assignee: Owen Mumford Limited, Oxford (GB)

( * ) Notice: Subject to any disclaimer, the term of this patent is extended or adjusted under 35 U.S.C. 154(b) by 278 days.

(21) Appl. No.: 10/089,834

(22) PCT Filed: Dec. 7, 2000

(86) PCT No.: PCT/GB00/04672

§ 371 (c)(1),
(2), (4) Date: Apr. 4, 2002

(87) PCT Pub. No.: WO01/41642

PCT Pub. Date: Jun. 14, 2001

(65) Prior Publication Data

US 2002/0151920 A1    Oct. 17, 2002

(30) Foreign Application Priority Data

Dec. 8, 1999   (GB) ................................. 9928876.3

(51) Int. Cl.
*A61B 17/34* (2006.01)
(52) U.S. Cl. ...................... 606/181; 600/583
(58) Field of Classification Search ......... 606/181–183
See application file for complete search history.

(56) References Cited

U.S. PATENT DOCUMENTS

| | | | | |
|---|---|---|---|---|
| 3,651,972 A | * | 3/1972 | Itoh | ........................... 215/295 |
| 5,304,193 A | | 4/1994 | Zhadanov | |
| 5,324,303 A | * | 6/1994 | Strong et al. | ............... 606/181 |
| 5,454,828 A | | 10/1995 | Schraga | |
| 5,984,940 A | * | 11/1999 | Davis et al. | ................ 606/181 |
| 6,210,420 B1 | * | 4/2001 | Mauze et al. | ................ 606/182 |

FOREIGN PATENT DOCUMENTS

| | | |
|---|---|---|
| DE | 197 18 081 A1 | 11/1998 |
| EP | 0 885 590 A1 | 12/1998 |

* cited by examiner

*Primary Examiner*—Julian W. Woo
*Assistant Examiner*—Sarah Webb
(74) *Attorney, Agent, or Firm*—Young & Thompson

(57) ABSTRACT

A lancet body (2) is integrally molded with a cap (3) for a firing device, the cap concealing the needle tip (5). the cap (3) can be used to insert the lancet (1), which is held while the cap is twisted off. The cap (3) is then fitted to the firing device to provide an apertured platform to be held against the skin and through which the needle tip (5) will momentarily project. The cap (3) has to be deformed to fit, and on being removed and recovering its natural shape internal lugs (14) catch hold of the released lancet (1) and remove that as well.

15 Claims, 2 Drawing Sheets

INTEGRATION OF A LANCETTE WITH ITS CAPTURING AND REMOVING CAP

BACKGROUND OF THE INVENTION

This invention relates to combined lancets and caps.

DESCRIPTION OF THE RELATED ART

Such a combination is described in U.S. Pat. No. 5,324,303. A lancet body is integrally moulded with a cap, initially to conceal the tip of a needle largely embedded in the lancet body. This renders the tip safe while the lancet is handled before use. The cap can be twisted off to reveal the needle tip and then fitted to the forward end of a firing device, with the lancet inserted. It provides a platform which is pressed against the user's skin and an aperture through which the needle tip is momentarily projected when the device is fired.

After use, the lancet should be disposed of safely since the needle will be contaminated. This can easily spread to the cap as well, and so that should be disposed of at the same time. The firing device is not at risk, and can be re-used indefinitely.

SUMMARY OF THE INVENTION

It is the aim of this invention to provide an arrangement where the removal of the cap also removes the lancet with its needle tip safely housed inside the cap, so that both can be thrown away together without exposure of the needle tip.

According to the present invention there is provided a combined lancet and cap for a lancet firing device to which the cap can be fitted to provide an apertured platform to bear against the user's skin and through which the tip of the lancet needle is momentarily projected when the device is fired, the cap and lancet body being integrally moulded in plastics material with the cap concealing the needle tip but being breakable away from the body to expose that tip, wherein the cap is moulded with a shape that requires manual deformation to fit the firing device and wherein, when removed after use, the cap reverts to its natural shape and thereby captures and removes the lancet with the needle tip safe within the cap.

In one preferred form the rear end of the cap is non-circular. Compression along its major axis will cause it to become circular to fit a firing device, cylindrical at its forward end at least. There are various possible modes of engagement, for example by screw thread, by a bayonet type fitting, or by snap-fitting.

Also in the preferred form, the interior of the cap has opposed projections on its minor axis and the lancet body has an abutment behind which the projections can engage when the cap is removed from a firing device and reverts to its natural shape but which is clear of the projections when the cap is deformed and fitted to a firing device. Assuming the rear end of the cap is elliptical, reducing the major axis increases the minor axis of the cross-section, thereby moving the projections outwardly where they do not interfere with the forward and reverse motion of the lancet.

It is also advisable for the lancet to have a further abutment to the rear of the first one, the projections engaging between the abutments when the cap is removed from a firing device. This will prevent the lancet moving forward sufficiently for the needle tip to be re-exposed through the front of the cap.

The lancet body should be non-rotative in the firing device. It can be inserted using the cap as a handle, the rear end of the lancet being receivable by a holder within the device. The cap is then twisted to break away from the lancet body. The lancet body and holder will conveniently be adapted to be retained in a retracted position within the firing device when the lancet is inserted. It will therefore be prevented from falling out accidentally before the cap is fitted, and it will be properly located for firing.

BRIEF DESCRIPTION OF THE DRAWINGS

For a better understanding of the invention, one embodiment will now be described, by way of example, with reference to the accompanying drawings, in which.

DESCRIPTION OF THE PREFERRED EMBODIMENTS

Figure 1:
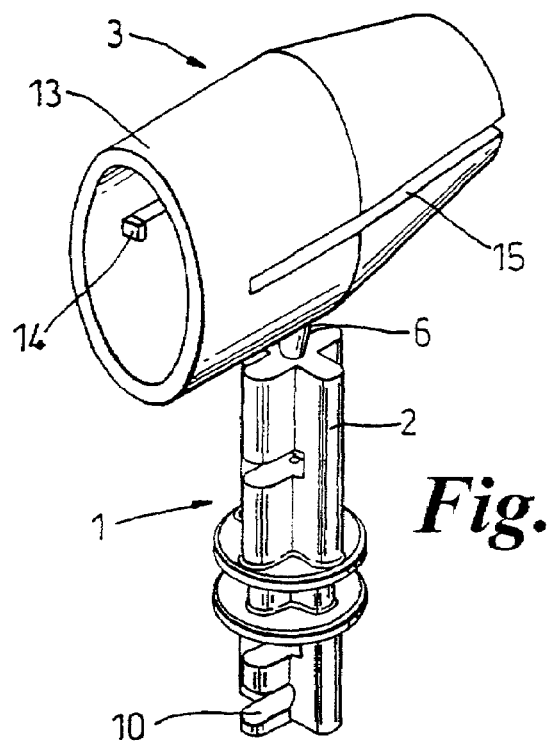
FIG. 1 is a perspective view of a combined lancet and cap.
Figure 2:
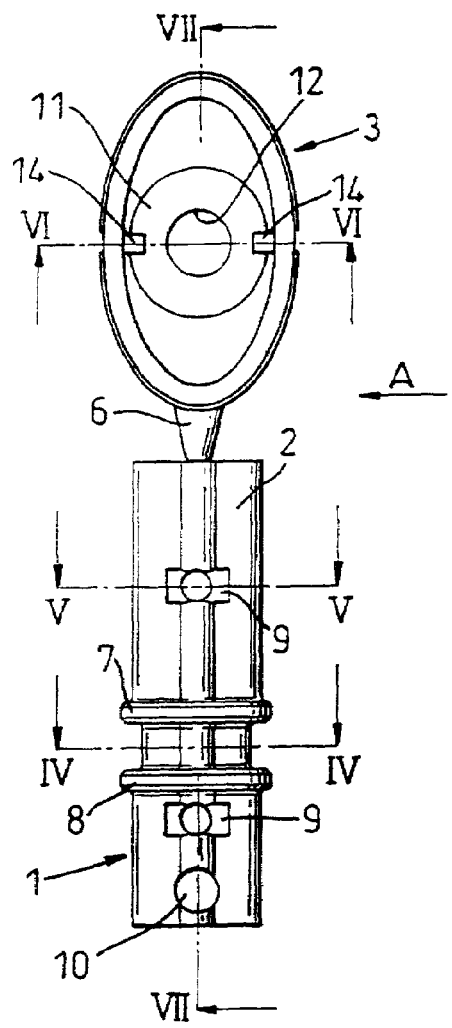
FIG. 2 is a side view of the lancet and cap.
Figure 3:
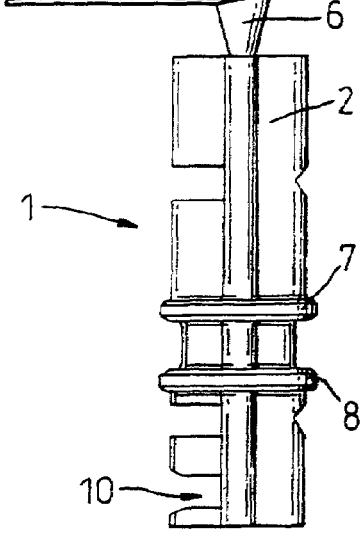
FIG. 3 is another side view of the lancet and cap in the direction A of FIG. 2.
Figure 4:
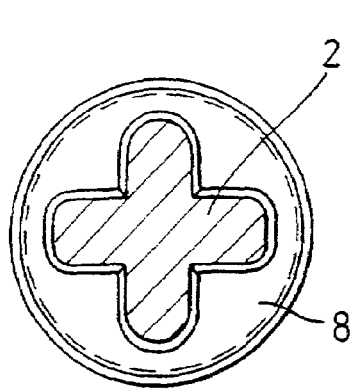
FIG. 4 is a section on the line IV—IV of FIG. 2.
Figure 5:
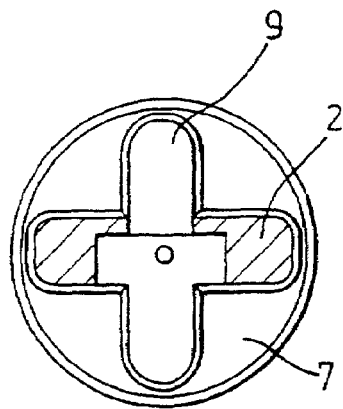
FIG. 5 is a section on the line V—V of FIG. 2.
Figure 6:
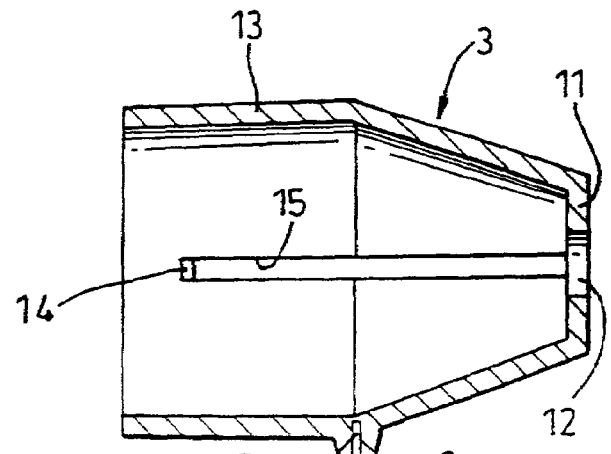
FIG. 6 is a section on the line VI—VI of FIG. 2.
Figure 7:
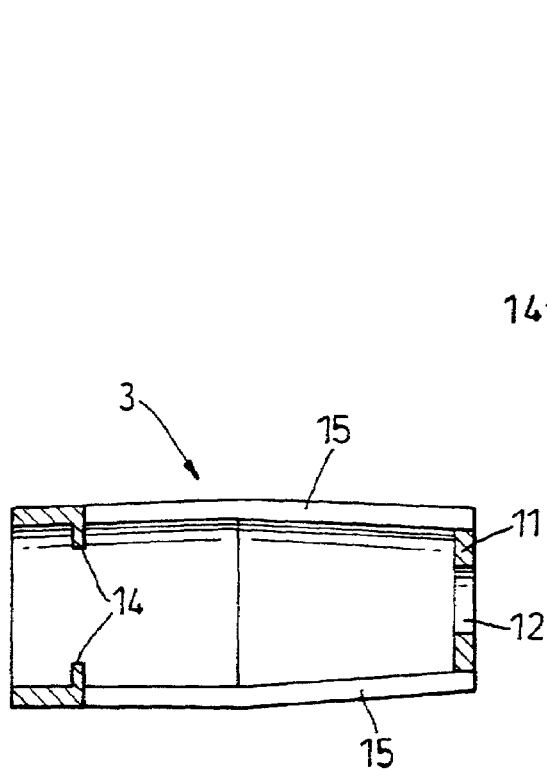
FIG. 7 is a section on the line VII—VII of FIG. 2.
Figure 7:
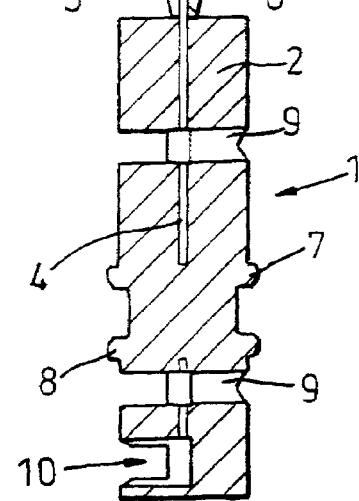

A lancet 1 has a plastics body 2 integrally moulded with a cap 3. The body 2 contains a needle 4 whose tip 5 projects into a neck 6 which connects the body 2 and the cap 3. The lancet is designed to be fired by a device (not shown) into whose forward end the cap 3 can fit.

The lancet 1 is mostly of cruciform shape throughout its length, but shortly beyond its mid-point from the cap 3 there are two axially spaced circular ribs 7 and 8 of a radius that makes them slightly proud of the cylindrical envelope of the rest of the body 2. There are various diametral and radial passages 9 and 10 left by the moulding process, are necessary for holding the needle 4.

The cap 3 is of cup-like form with a circular base 11 having a central aperture 12. From the rim of the base 11 it flares outwardly, developing into an elliptical cross-section, and at about the mid-length there is a break into a portion 13 of constant elliptical cross-section. The neck 6 is situated at this break. Internally of this portion 13 there are two opposed lugs 14 on the minor axis of the elliptical cross-section. These are at the ends of longitudinal slots 15 extending from the base 11 which are necessary for simplifying the mould.

For use, the lancet 1 and cap is inserted rear end first into the cylindrical forward end of a firing device using the cap 3 as a handle. The lancet is captured within the device by means of interference between its rear end and a spring-loaded, cup-like lancet holder. It is held against rotation by the action of internal ribs within the lancet holder engaging with the cruciform shape of the lancet body. The lancet holder itself is held against rotation but can of course move longitudinally of the firing device when released. The action of pushing the lancet in may retract the holder to a cocked position, where it is held by a trigger device. The cap 3 is then twisted, and this breaks it away from the lancet body 2 at the narrowest point of the neck 6, leaving the tip of the needle 5 exposed. The large open end portion 13 of the cap 3 is then presented to the forward end of the firing device, the portion 13 being squeezed along the major axis of the elliptical cross-section. The nature of the plastics material and its thickness allow it to be deformed into a circular cross-section. It can then enter the forward end of the firing device and, for example, screw into it. But as mentioned above, there are other forms of engagement.

The device is used by placing the base 11, serving as a platform, against the skin, and firing the lancet so that the needle tip momentarily projects through the aperture 12. The lancet bounces back so that the tip is safely within the cap. The lugs 14 are then opposite or possibly slightly to the rear of the gap between the ribs 7 and 8. The cap is removed and, if it is an unscrewing action, the length of the thread is such that the lugs 14 will remain in or come into registry with the gap between the ribs 7 and 8 as the cap comes clear. Alternatively, if the lancet cap 3 is clipped into the front of the firing device then it may be removed by sliding an ejector of the device forwards, which then acts on the edge of the open end portion 13 of the cap, pushing it away from the device. As the cap is freed from whatever engagement it had with the firing device the portion 13 immediately reverts to its elliptical cross-section and the lugs 14 close towards each other and engage between the ribs 7 and 8. The lancet 1 is therefore captured by the cap 3 with the needle tip safely inside. The cap is lightly pulled by the rib 7 to unplug the lancet 1 from the spring-loaded holder and it can then be thrown away with the lancet attached as a single item. The rib 8 stops the lancet moving forwards within the cap sufficiently to re-expose the needle tip 5 through the aperture 12.

With the lancet shown, the cap is intended to fit within the forward end of the firing device. But with some re-design, bringing the ribs 7 and 8 forwards, and making the lugs 14 more prominent as well as having them not so far back, a cap could be made to fit (with the necessary preliminary distortion) outside the firing device.

What is claimed is:

1. A lancet, comprising:
    a body;
    a neck located at a first end of the body;
    a cap connected to the body at the neck and integrally moulded with the body,
    the cap being of a cup form with, at a front end, a base having a central aperture,
    an exterior surface of the cap flaring outwardly from the base into an approximately elliptical cross-section at a break circumference,
    the exterior surface extending beyond the break circumference, to a rear end of the cap, as a constant approximately elliptical cross-section portion,
    two axially spaced ribs located on the body and defining a gap therebetween;
    two inwardly-directed opposed lugs, limited in position to an internal part of the constant approximately elliptical cross-section portion, the two inwardly-directed opposed lugs located on an inner surface of the constant approximately elliptical cross-section portion on the minor axis thereof; and
    a needle with a tip projecting into the neck, wherein,
    the rear end of the cap connects to a cylindrical forward end of a firing device by squeezing the constant approximately elliptical cross-section portion along the major axis of the approximately elliptical cross-section to deform the approximately elliptical cross-section into a circular cross-section,
    upon firing the lancet the needle tip momentarily projects through the aperture and then retracts so that the needle tip is within the cap and the opposed lugs are proximate the gap between the two ribs, and
    upon removal of the firing device from the cap, the constant approximately elliptical cross-section portion resumes the approximately elliptical cross-section with the opposed lugs closing towards each other and engaging the gap between the two ribs to capture the ribs and to capture the body within the cap.

2. The lancet of claim 1, wherein,
    two opposed longitudinal slots originate at the two opposed lugs and extend to the rim of the base.

3. The lancet of claim 1,
    wherein, a first of the two ribs defines a first abutment, and a second of the two ribs defines a second abutment to the rear of the first abutment, the lugs being adapted to engage between the first and second abutments when the cap is removed from a firing device.

4. The lancet of claim 1, in combination with a firing device wherein the rear of the lancet body is non-rotatively receivable by a holder in the firing device.

5. A lancet, comprising:
    a body with a neck located at a first end;
    a cap connected to the body at the neck,
    the cap having a front end with a base having a central aperture,
    an exterior surface of the cap flaring outwardly into an approximately elliptical cross-section at a break circumference,
    the exterior surface extending beyond the break circumference, to a rear end of the cap, as a constant approximately elliptical cross-section portion, a portion of the exterior surface extending to the rear of the cap being a continuous wall;
    a gap located between two axially spaced circular ribs of the body, the ribs extending beyond a cylindrical envelope of remaining portions of the body;
    two opposed lugs extending inwardly from an internal part of the constant approximately elliptical cross-section portion, the two opposed lugs located on the minor axis of the constant approximately elliptical cross-section portion;
    two opposed longitudinal slots originating at the two opposed lug and extending to the rim of the base; and
    a needle with a tip projecting into the neck, wherein,
    the rear end of the cap connects the cap to a cylindrical forward end of a firing device by squeezing the constant approximately elliptical cross-section portion along the major axis of the approximately elliptical cross-section to deform the approximately elliptical cross-section into a circular cross-section corresponding to the cylindrical forward end of the firing device,
    upon firing the lancet the needle tip momentarily projects through the aperture and then retracts so that the needle tip is within the cap and the opposed lugs are proximate the gap between the two ribs, and
    upon removal of the firing device from the cap, the constant approximately elliptical cross-section portion resumes the approximately elliptical cross-section with the opposed lugs closing towards each other and engaging the body at the gap between the ribs to capture the body within the cap.

6. The lancet of claim 5, wherein, the body has a cruciform cross section.

7. A lancet, comprising:
    a body holding a needle;
    a cap connected to the body at a neck, the cap concealing a tip of the needle and being breakable away from the body at the neck to expose the tip,
    the cap having a front end with a base having a needle aperture, an exterior surface of the cap flaring outwardly from the base into an approximately elliptical cross-section at a break circumference, the exterior surface extending beyond the break circumference, to a rear end of the cap, as a constant approximately elliptical cross-section portion;

a gap located between two axially spaced circular ribs of the body, the ribs extending beyond a cylindrical envelope of remaining portions of the body;

two opposed lugs extending inwardly from an internal part of the constant approximately elliptical cross-section portion; and two opposed longitudinal slots originating at the two opposed lug and extending toward the rim of the base, and, wherein, the rear end of the cap connects the cap to a cylindrical forward end of a firing device by squeezing the constant approximately elliptical cross-section portion along the major axis of the approximately elliptical cross-section to deform the approximately elliptical cross-section into a circular cross-section corresponding to the cylindrical forward end of the firing device, upon firing the lancet the needle tip momentarily projects through the aperture and bounces back so that the needle tip is within the cap and the opposed lugs are proximate the gap between the two ribs, and upon removal of the firing device from the cap, the constant approximately elliptical cross-section portion resumes the approximately elliptical cross-section with the opposed lugs closing towards each other and engaging the body at the gap between the ribs to capture the body within the cap, the cap, removed from body, configured to have the lugs co-operate with the ribs to lock the cap on the lancet.

8. The lancet of claim 7, wherein, the body has a cruciform cross section.

9. The lancet of claim 1, wherein, the cap, removed from body, is configured to have the lugs co-operate with the ribs to lock the cap on the lancet.

10. The lancet of claim 5, wherein, the cap, removed from body, is configured to have the lugs co-operate with the ribs to lock the cap on the lancet.

11. The lancet of claim 1, wherein, manual removal of the cap automatically removes the lancet, the cooperation of the lugs and ribs performing a capture, an extraction, and a locking as the cap is pulled off the firing device.

12. The lancet of claim 5, wherein, removal of the cap, by a manual pulling operation, automatically removes the lancet, the co-operation of the lugs and ribs performing a capture, an extraction, and a locking as the cap is pulled off the firing device.

13. The lancet of claim 7, wherein, removal of the cap automatically removes the lancet, the co-operation of the lugs and ribs performing a capture, an extraction, and a locking as the cap is pulled off the firing device.

14. The lancet of claim 1, wherein, a portion of the exterior surface of the cap extending to the rear of the cap being a continuous wall.

15. The lancet of claim 7, wherein, a portion of the exterior surface of the cap extending to the rear of the cap being a continuous wall.

* * * * *